(12) United States Patent
Giri

(10) Patent No.: US 6,767,716 B2
(45) Date of Patent: Jul. 27, 2004

(54) CHEMLUMINESCENT SYSTEMS CONTAINING UNSATURATED 1,2-DIOXETANES

(76) Inventor: Brij P. Giri, 36725 Lamarra Dr., Sterling Heights, MI (US) 48310

( * ) Notice: Subject to any disclaimer, the term of this patent is extended or adjusted under 35 U.S.C. 154(b) by 109 days.

(21) Appl. No.: 09/883,586

(22) Filed: Jun. 18, 2001

(65) Prior Publication Data

US 2002/0013250 A1 Jan. 31, 2002

Related U.S. Application Data

(60) Provisional application No. 60/212,883, filed on Jun. 17, 2000.

(51) Int. Cl.⁷ .................................................. C12Q 1/44
(52) U.S. Cl. .......................... 435/19; 549/220; 549/221
(58) Field of Search ............................. 435/19, 4, 960; 252/700; 436/172; 549/200, 221, 332

(56) References Cited

U.S. PATENT DOCUMENTS

| | | | | |
|---|---|---|---|---|
| 4,956,477 A | * | 9/1990 | Bronstein et al. | 549/221 |
| 5,547,836 A | * | 8/1996 | Bronstein et al. | 425/6 |
| 5,631,167 A | * | 5/1997 | Adolfsen et al. | 436/53 |
| 5,637,747 A | * | 6/1997 | Bronstein et al. | 558/194 |
| 5,756,770 A | * | 5/1998 | Bronstein et al. | 549/220 |
| 5,777,135 A | * | 7/1998 | Akhavan-Tafti et al. | 549/332 |
| 6,461,876 B1 | * | 10/2002 | Giri | 436/546 |

FOREIGN PATENT DOCUMENTS

WO    WO 97/24460    *   7/1997

OTHER PUBLICATIONS

Schaap A. Paul. Chemical and Enzymatic Triggering of 1,2–Dioxetanes. Office of Naval Research NR 051–840, Technical Report #3, Mar. 1987.*

* cited by examiner

Primary Examiner—Ralph Gitomer
(74) Attorney, Agent, or Firm—The Weintraub Group, P.L.C.

(57) ABSTRACT

A chemiluminescent 1,2-dioxetane includes an alkaline phosphatase triggerable stable 1,2-dioxetane; a polymeric enhancer which is either an ammonium or phosphonium salt of a polyvinylbenzyl chloride and an aqueous enzyme diluent or stabilizer which corresponds to blood component including blood protein. The system is efficacious for single molecule detection of alkaline phosphatase and other enzymes.

11 Claims, 5 Drawing Sheets

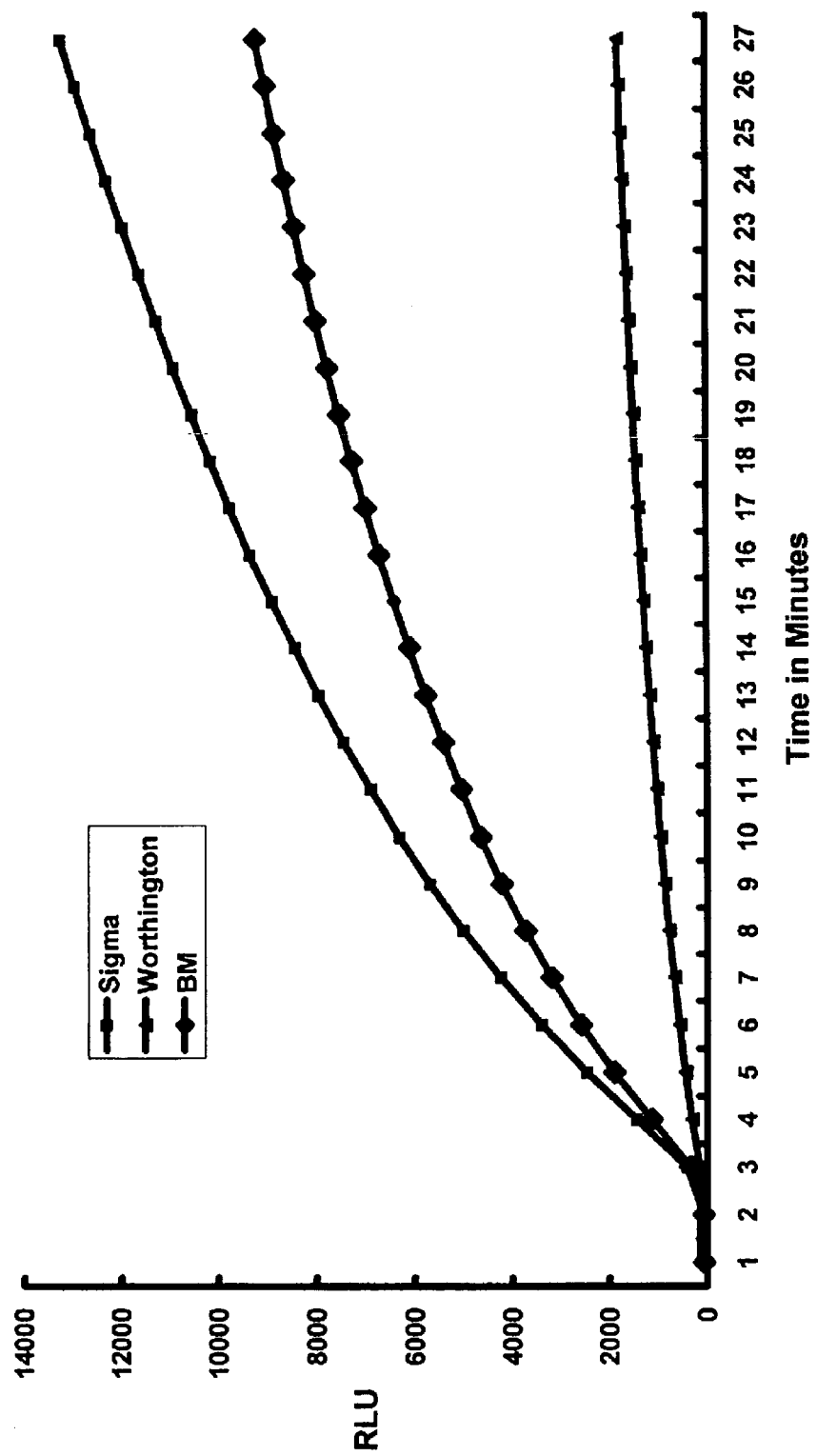

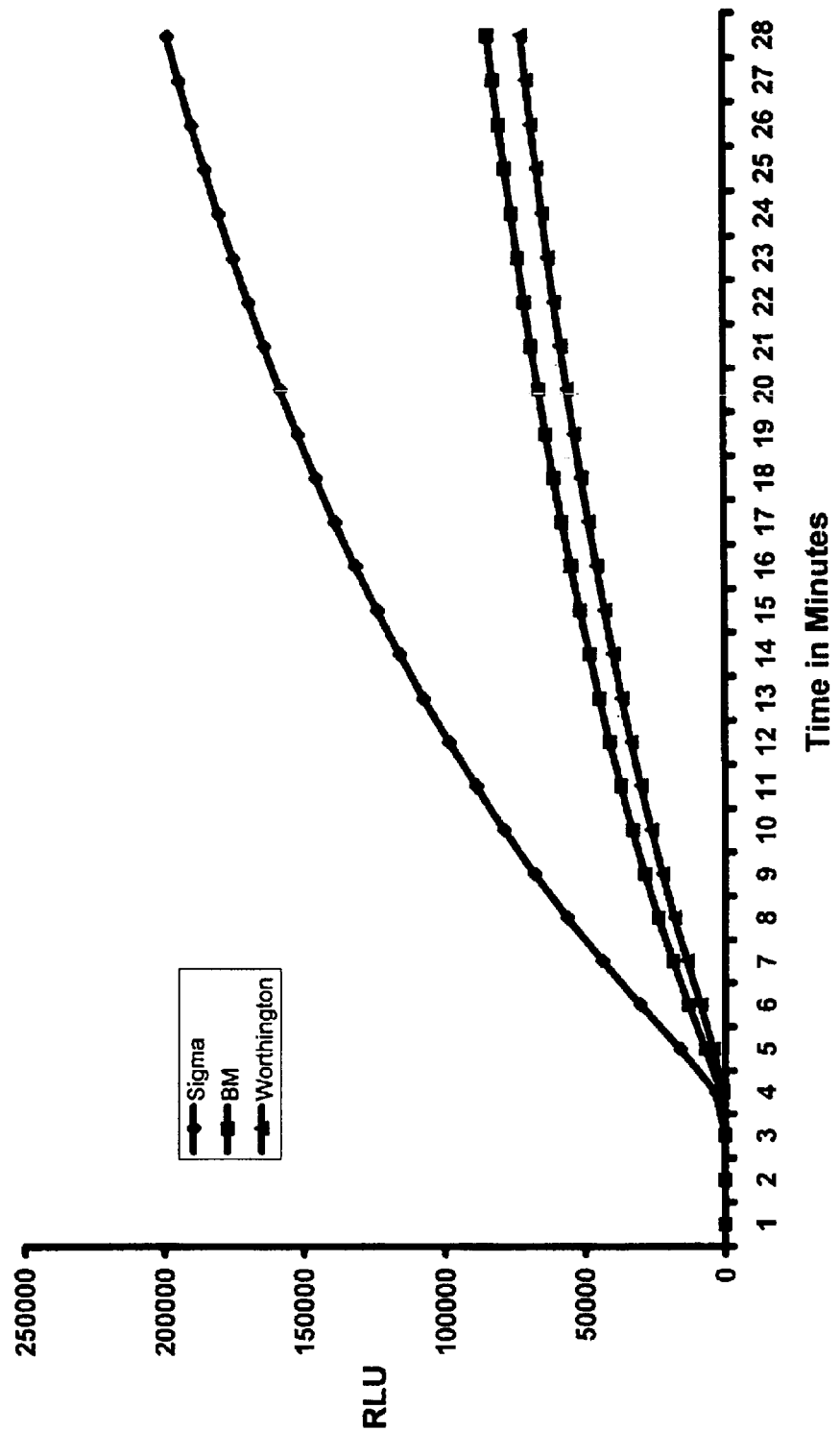

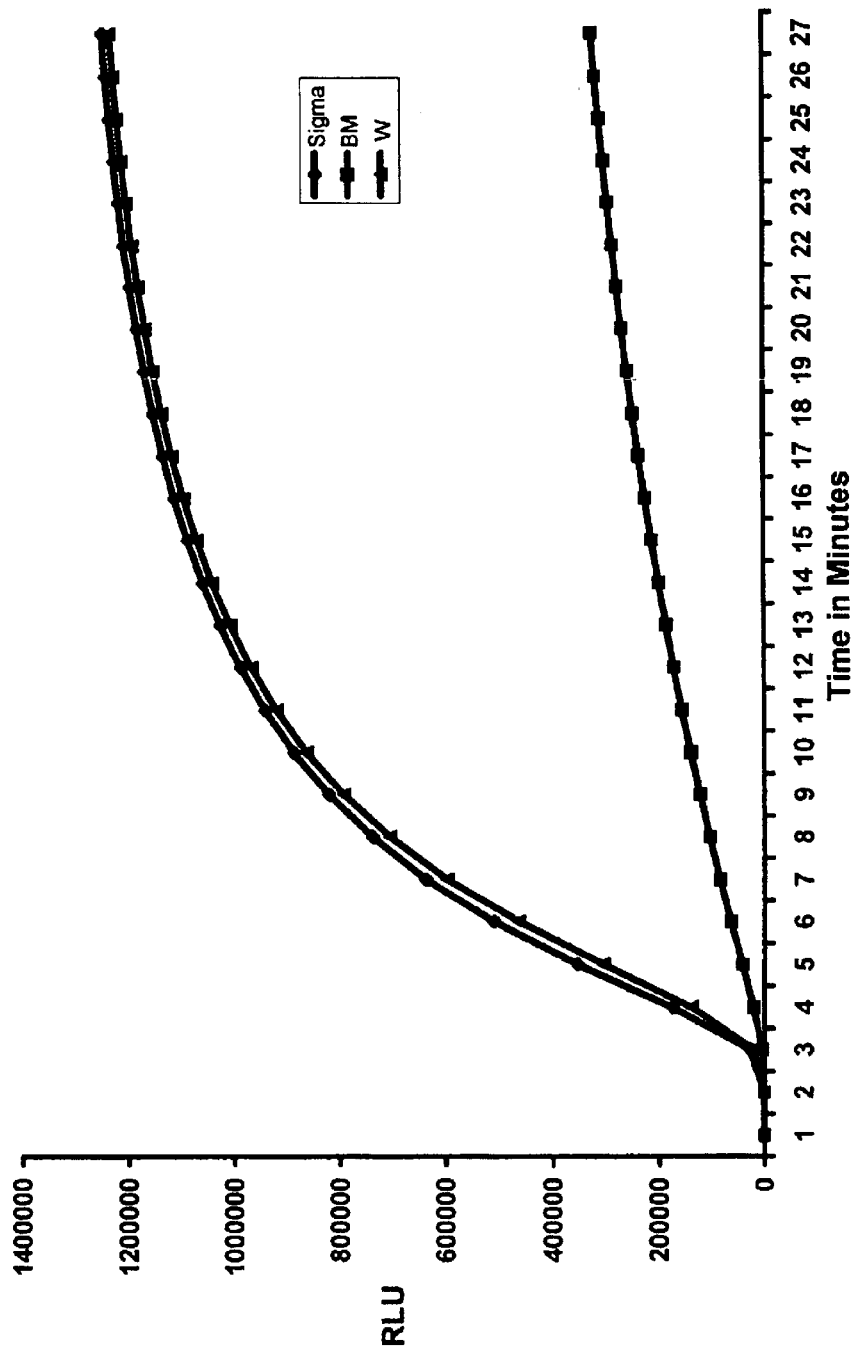

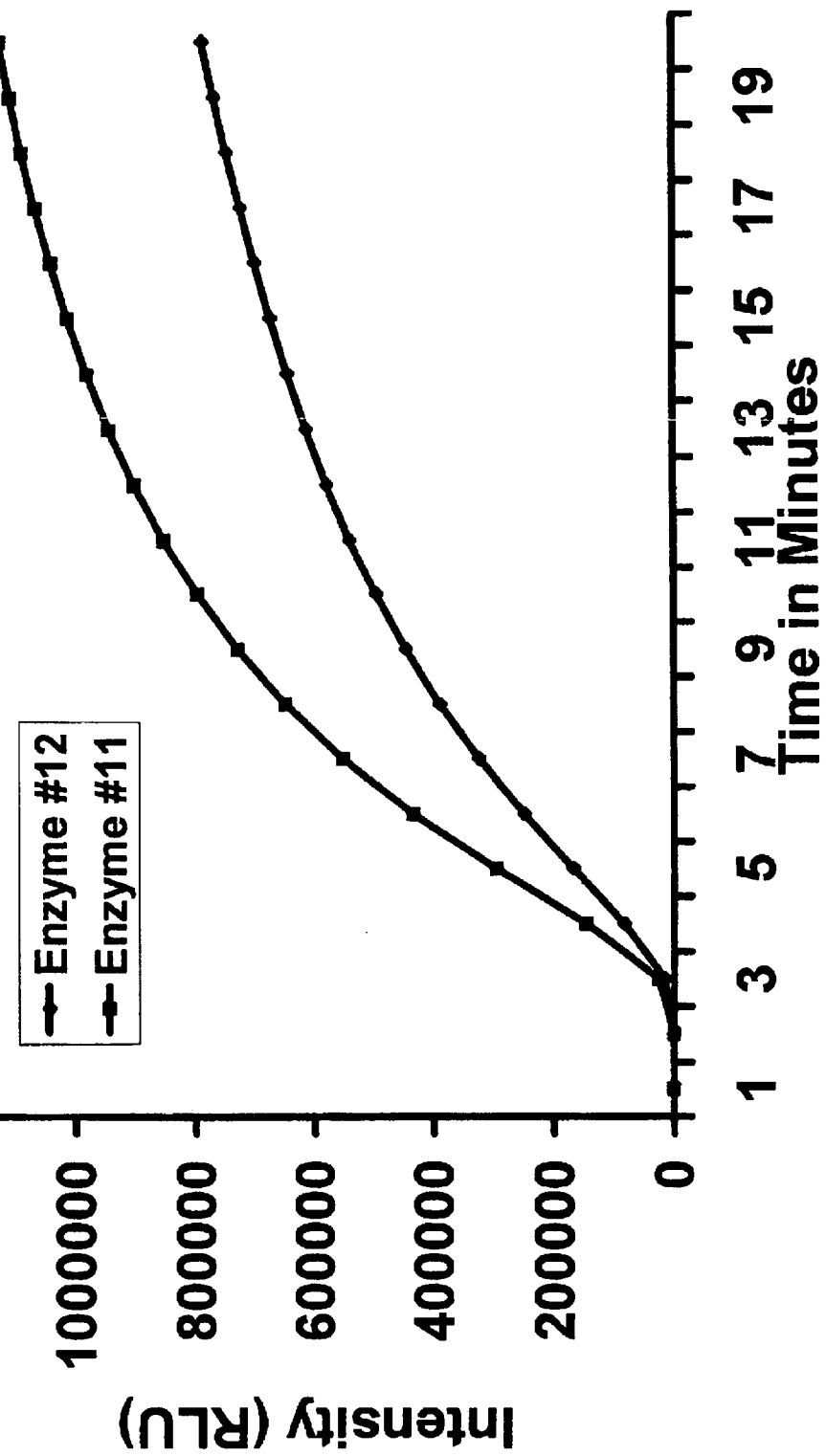

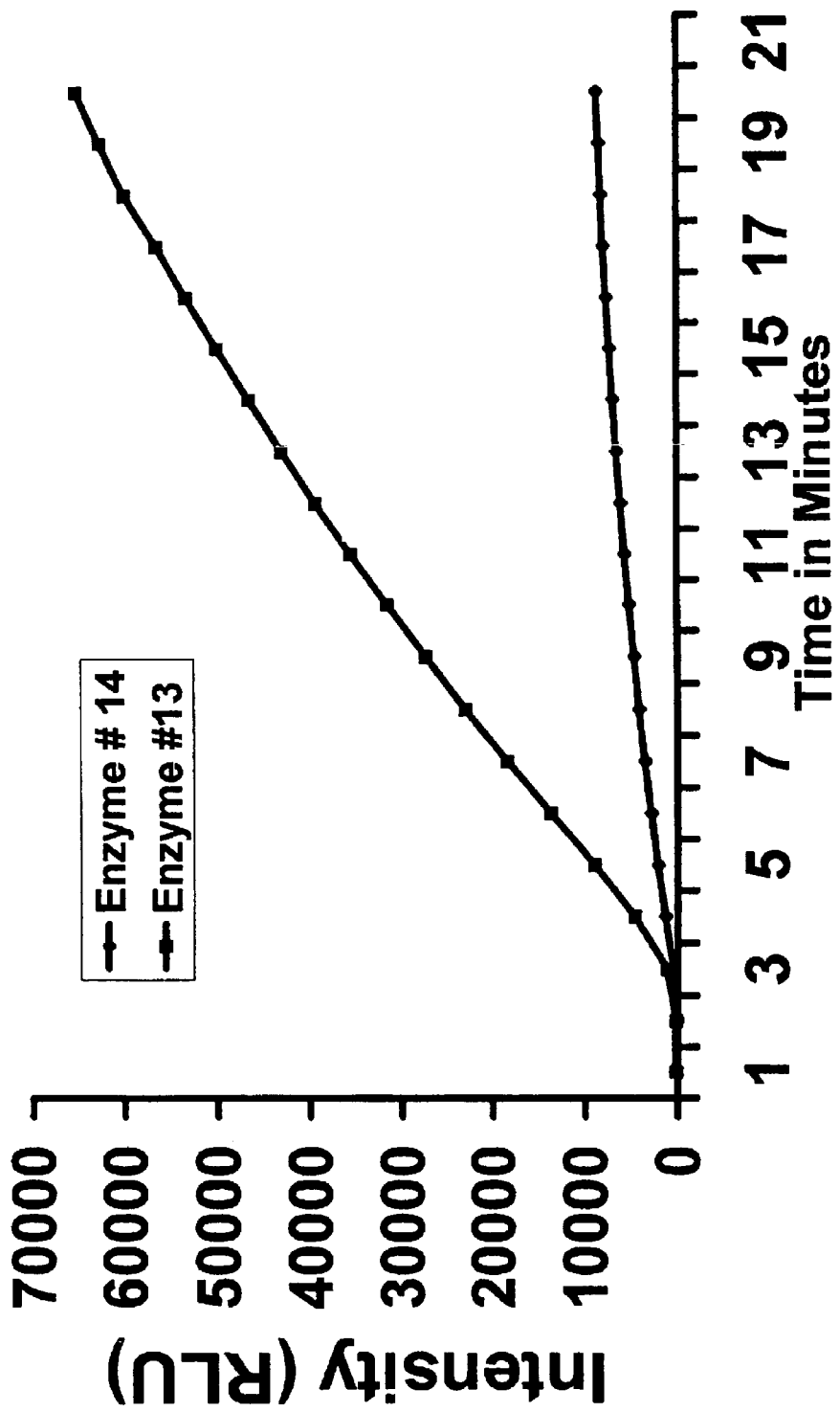

CHEMLUMINESCENT SYSTEMS CONTAINING UNSATURATED 1,2-DIOXETANES

CROSS REFERENCE TO RELATED APPLICATIONS

This application is a completion application of co-pending U.S. Provisional Application Serial No. 60/212,883, filed Jun. 17, 2000, the disclosure of which is hereby incorporated by reference

BACKGROUND OF THE INVENTION

1. Field of the Invention

The present invention relates to enhanced chemiluminescence of 1,2-dioxetane compounds, derived from the oxidation of novel alkenes prepared by the coupling of substituted aromatic esters or ketones and spiro-fused ketones with or without a π-electron system or a carbon—carbon double bond, in the presence of water-insoluble or partially water-soluble or water-soluble polymers obtained from natural or synthetic sources. More particularly, the present invention relates to a 1,2-dioxetane chemiluminescent system which can achieve a detection level as low as an attogram of enzyme or "single molecule" detection. Even more particularly, the present invention relates to a 1,2-dioxetane chemiluminescent system which includes (1) a stabilized dioxetane which can be destabilized from alkaline phosphatase or other enzymes and emit light on decomposition, (2) an enhancer for enhancing the light intensity to a maximum limit, and (3) an enzyme diluent or buffer that stabilizes the enzyme for extended periods of time during the reaction and does not effect the efficiency of the enhancer and the 1,2-dioxetane, and methods of use thereafter

2. Prior Art

Chemiluminescence and bioluminescence have been tested as potential replacements for radioactive labels, not only in competitive and sandwich-type immunoassays but, also, in DNA sequencing and other related research. Chemiluminescence is advantageous also for detecting and measuring trace elements and pollutants for environmental control. Thus, research on the chemiluminescence of organic compounds is an on-going area of major emphasis. Chemiluminescence provides a major advantage since it generates cold light, i.e. its generated light is not caused by vibrations of atoms and/or molecules involved in the reaction, but by direct transformation of chemicals into electronic energy. The best known chemiluminescent reactants are stabilized 1,2-dioxetanes, acridanes, acridinium esters, luminol, isoluminol and derivatives thereof, and lucigenen.

Stabilized 1,2-Dioxetanes

Chemiluminescent compounds, their preparation and their uses have been long documented in the prior art. These "high energy" molecules store sufficient energy to generate, on fragmentation, electronically excited carbonyl products which are responsible for the observed chemiluminescence. Dioxetanes and, especially, 1,2-dioxetanes are eminently useful to detect the presence, as well as the absence, of certain enzymes in fluids such as blood and the like because of their chemiluminescence. Thus, 1,2-dioxetanes are eminently useful in doing medical assays.

Generally, 1,2-dioxetanes are thermally labile substances having a wide range of stability and which decompose on heating to emit light according to the following reaction:

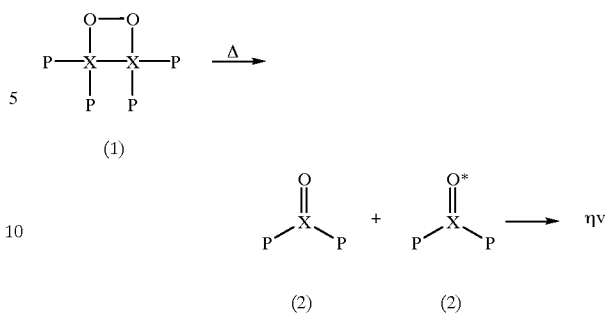

where each R corresponds to any one of a multitude of organic moieties widely reported in the prior art, as detailed herebelow. As noted these 1,2-dioxetanes have a wide range of stability. For example, the prior art, as found in: (a) K. W. Lee, L. A. Singer and K. D. Legg, J.Org.Chem., 41, 2685 (1976); (b) F. McCapra, I. Beheshti, A. Burford, R. A. Hanu and K A. Zakika, J.Chem.Soc., Chem.Commun.,944(1977); and (c) J. H. Wieringa, J. Strating, H. Wynberg and W. Adam, Tet. Lett.,169 (1972); respectively, disclose the following 1,2-dioxetanes of different stability:

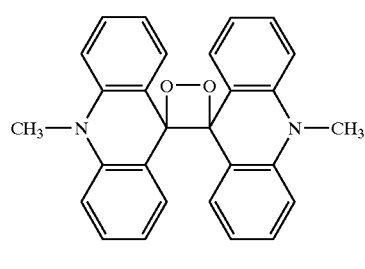

EA@18Kcal/mol (3)

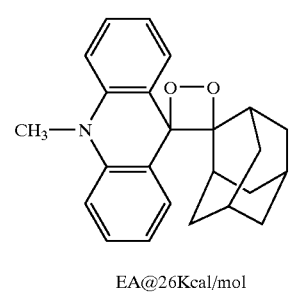

EA@26Kcal/mol (4)

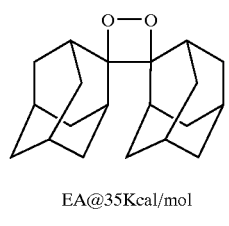

EA@35Kcal/mol (5)

Although these high energy compounds are all spiro-substituted 1,2-dioxetanes. Spiroadamantane substitution exerts a tremendous stabilizing effect on these four-membered ring peroxides. The lower activation energy (EA)

of the dioxetanes of formulae (3) and (4) is explained by the donation of charge from nitrogen to the dioxetane ring. The dioxetane of formula (5) decomposes at 150° C. and has a half-life, at 25° C., of more than 20 years.

A stabilized 1,2-dioxetane (6) below, dispiro[adamantane-2,3'-[1,2-dioxetane]-4,9-fluorene] was isolated as crystals and described by W. Adam and L. A. A. Encarnacion, Chem. Ber.,115, 2592 (1982).

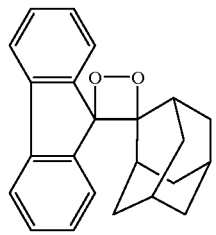

(6)

The stability of 1,2-dioxetanes (5) and (6) is described on the basis of the bulky and rigid spiro nature of the adamantane group.

The first stable and enzymatic triggerable 1,2-dioxetane was synthesised by the oxidation of (6-acetoxy-2-naphthyl) methoxy methyleneadamantane as reported by A. P. Schaap, R. S. Handley and B. P. Giri, Tet. Lett., 935 (1987). This 1,2-dioxetane utilizes aryl esterase emzyme to catalyze the cleavage of the acetate group of a naphthylacetate-substituted-1,2-dioxetane and produce chemiluminescence in aqueous buffers at ambient temperature by the following sequence:

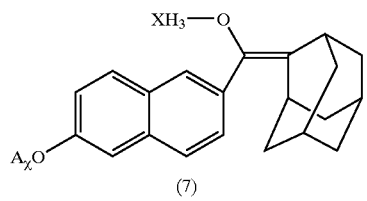

(7)

Σενοττοξ
Ατγητ, O₂

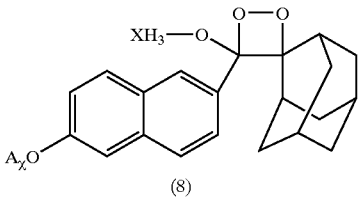

(8)

Αρψλεστρασε

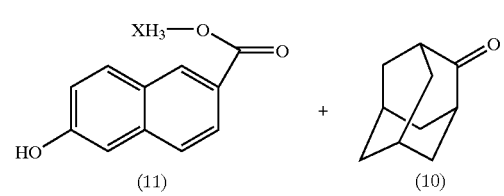

(11) (10)

+ hn ←

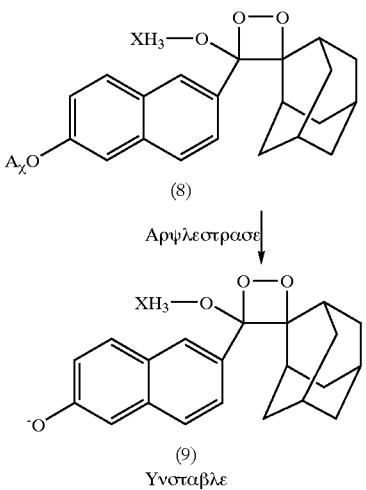

(9)
Υνσταβλε

Several other stabilized 1,2-dioxetanes and their use as enzyme substrates have been disclosed in the literature. See, inter alia, A. P. Schaap, T. S. Chen, R. S. Handley, R. DeSilva and B. P. Giri, Tet. Lett., 1155(1987); A. P. Schaap, M. D. Sandison and R. S. Handley, Tet. Lett., 1159 (1987); U.S. Pat. No. 4,962,192; U.S. Pat. No. 4,978,614; U.S. Pat. No. 5,386,017; U.S. Pat. No. 5,721,370, other useful 1,2-dixetanes are described in the copending patent apply, the disclosures of which are hereby incorporated by reference.

These several other 1,2-dioxetanes, generally, have the following general structures:

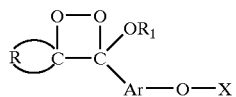

(12)

wherein

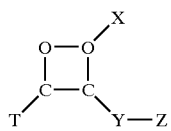

is a non-active site, i.e. non-reactive and which is selected from the group of polycyclic alkyl groups containing 6 to 30 carbon atoms, OX is an oxy group substituted on an aryl ring which forms an unstable oxide intermediate 1,2-dioxetane compound when triggered to remove X by an activating agent, and X is a chemically labile group which is removed by the activating agent to form light and carbonyl containing compounds, R₁ is a lower alkyl containing 1 to 8 carbon atoms, or mixtures thereof, or

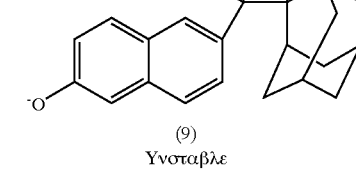

(13)

wherein T is a non-active site which is a cycloalkyl or a polycycloalkyl group bonded to the 4-membered ring portion of the dioxetane by a spiro linkage; Y is a fluorescent chromophore; X is hydrogen, alkyl, aryl arylkyl, alkaryl, heteroalkyl, heteroaryl, cycloalkyl, cycloheteroalkyl or an enzyme cleavable group, and Z is hydrogen or an enzyme cleavable group, provided that at least one of X or Z must be an enzyme cleavable group, or

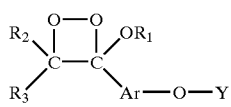

(14)

wherein, (1) when Ar—O—Y and OR join together to give an aryl group substituted with an O—Y group to form a stable 1,2-dioxetane intermediate which is triggerable to form an unstable intermediate oxide, $R_2$ and $R_3$ either form (a)

which is either cyclic, polycyclic or a spiro-fused ring containing at least one carbon—carbon double bond or cabon—carbon triple bond in the ring or side chain with or without hetero atoms, or (b)

which is either cyclic, polycyclic or a spiro-fused ring containing a substituted or unsubstituted fused aromatic ring or substituted or unsubstituted aromatic ring attached by linker arms;

(2) when Ar—O—Y and $OR_1$ do not join together a) Ar is an aryl which may be phenyl, substituted phenyl, naphthyl, substituted naphthyl, anthryl, substituted anthryl and the like as well as a nonaromatic fluorescent or nonfluorescent group; Y is hydrogen, alkyl, acetate, t-butyldimethylsilyl or an enzyme or a group of enzymes cleavable group, or an antibody cleavable group; $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, linear or branched halogenated alkyl, alkylalcohol, alkylnitrile, alkylamine, alkylacid or an inorganic salt thereof, haloalkylalcohol, haloalkylnitrile, haloalkylamine, haloalkylacid or an inorganic salt, thereof, linker-flourescent molecule, linker-antibodies, linker-antigen, linker-biotin, linker-avidin, linker-protein, linker-carbohydrates or linker-lipids; $R_2$ and $R_3$ form either (i)

which is cyclic, polycyclic or a spiro-fused ring containing at least one carbon—carbon double bond or cabon—carbon triple bond in the ring or side chain with or without heteroatoms, or (ii)

(ii)

which is cyclic, polycyclic or a spiro-fused ring containing substituted or unsubstituted fused aromatic ring or substituted or unsubstituted aromatic rings attached by linker arms;

(b) Ar is an aryl which may be phenyl, substituted phenyl, naphthyl, substituted naphthyl, anthryl, substituted anthryl and the like or a nonaromatic fluorescent or nonfluorescent group; Y is a hydrogen, alkyl, acetate, t-butyldimethylsilyl or an enzyme or a group of enzymes cleavable group, or an antibody cleavable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, linear or branched halogenated alkyl, alkylalcohol, alkylnitrile, alkylamine, alkylacid or an inorganic salt thereof, haloalkylalcohol, haloalkylnitrile, haloalkylamine, haloalkylacid or an inorganic salt, thereof, linker-flourescent molecule, linker-antibodies, linker-antigen, linker-biotin, linker-avidin, linker-protein, linker-carbohydrate or linker-lipids; and $R_2$ and $R_3$ form

which is either a cyclic or polycyclic alkyl group or a spiro-fused ring with or without substitution or (c) Ar is an aryl which may be phenyl, substituted phenyl, naphthyl, substituted naphthyl, anthryl, substituted anthryl or and the like or a nonaromatic fluorescent or nonfluorescent group; Y is a hydrogen, alkyl, acetate, t-butyldimethylsilyl or an enzyme or a group of enzymes-cleavable group, or an antibody cleavable group; $R_1$ is selected from the group consisting of alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, linear or branched, alkylalcohol, alkylnitrile, alkylamine, alkylacid or an inorganic salt thereof, haloalkylalcohol, haloalkylnitrile, haloalkylamine, haloalkylacid (mono or dibasic) or an inorganic salt, thereof, a linker-fluorescent molecule, linker-antibodies, linker-antigen, linker-biotin, linker-avidin, linker-protein linker-carbohydrate or linker-lipid; and $R_2$ and $R_3$ are branched alkyl or cycloalkyl groups containing 3 to 8 carbon atoms and which can contain halogens and hetero atoms in the ring or side chain thereof.

The activation agent is selected from the group consisting of an acid, a base, a salt, an enzyme and an inorganic or organic catalyst, and electron donor source, Among, the useful and known commercially available enzyme-cleavable 1,2-dioxetanes, are those which correspond to the formulae shown below and are used in Immuno assays, Southern blotting, Northern blotting, Western blotting, Plaque/Colony lifts and DNA sequencing.

(15)

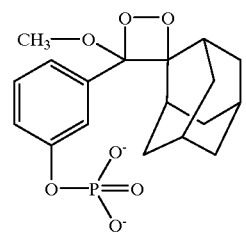

(16)
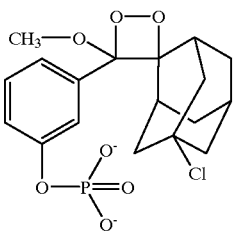

(17)
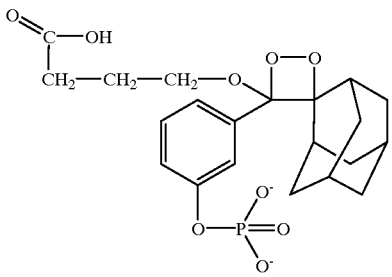

(18)
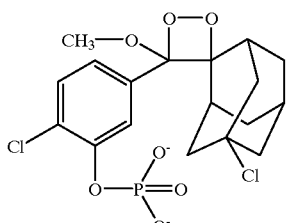

(19)
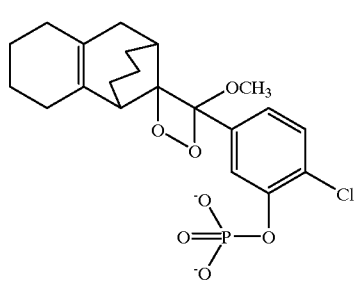

Enzymatic triggerable 1,2-dioxetanes such as those described by A. P. Schaap, R. S. Handley and B. P. Giri. *Tetrahedron Lett.*, 935 (1987); A. P. Schaap, T. S. Chen, R. S. Handley, R. DeSilva, and B. P. Giri, *Tetrahedron Lett.*, 1159 (1987) as well as in U.S. Pat. No. 5,707,550 are superior in immunoassays and other related applications compared to peroxidase substrates such as luminol and others. Stabilized 1,2-dioxetane substrates provide high signal, low background, wide dynamic range, rapid results and excellent reproducibility. These 1,2-dioxetanes provide substrates which are highly sensitive but can detect an enzyme concentration up to $10^{-21}$M ($6 \times 10^2$ molecules of alkaline phosphatase) in solution as well as on a membrane. The Comparative detection limit of alkaline phosphatase using fluorescence, time-resolved fluorescence and calorimetric techniques are $10^{-19}$ M ($6 \times 10^4$ molecules), $3 \times 10^{-19}$ M ($1.8 \times 10^5$ molecules) and $5 \times 10^{-17}$ M ($3 \times 10^8$, molecules), respectively.

Still other useful 1,2-dioxetanes are those disclosed in the copending PCT Application Serial No. U.S. patent application Ser. No. US99/20590 filed Sep. 8, 1999, the disclosure of which is hereby incorporated by reference.

While all of the prior art 1,2-dioxetanes compounds enumerated above provide enzyme cleavable 1,2-dioxetanes, it has been observed that in an aqueous buffer, the luminescence of these molecules is particularity poor, especially when trace amounts of biological materials are sought to be detected.

Enhancers

Numerous enhancers have been employed in conjunction with the use of stabilized 1,2-dioxtanes. The enhancement of chemiluminescence from a stable 1,2-dioxetane triggered decomposition by an enzyme in the presence of water soluble substances including a long chain aliphatic ammonium surfactant and a fluorescent compound has been reported in the literature (U.S. Pat. No. 4,959,182). Micelles containing cetyltrimethylammonium bromide(CTAB) and a fluorescent molecule attached to a long chain hydrocarbon, 5-(N-tetradecanoyl) aminofluorescein, capture the intermediate hydroxy-substituted 1,2-dioxetane, which is destabilized under basic pH of a buffer to decompose, thus leads to a 400-fold increase in chemiluminescence efficiency. Enhancement occurs by virtue of an efficient intermolecular energy transfer process from the anionic form of the excited state ester to the fluorescent compound, which is held in close proximity, and the hydrophobic environment of the surfactant.

Water-soluble polymeric quaternary ammonium salts alone or admixed with fluorescein as disclosed in (U.S. Pat. Nos. 4,978,614; 5,145,772; 5,547,836; 5,593,828, 5,654, 154) and polyvinylbenzyltrialkylphosphonium salts dissolved alone or covalently attached to fluorescent molecules as described in (U.S. Pat. Nos. 5,393,479; 5,431,845; 5,474,725; 5,582,775) have been taught to enhance of chemiluminescent efficiency of stable 1,2-dioxetanes.

The synthesis of polymeric quaternary ammonium compounds and polymeric benzyltrialkylphosphonium salts is well known in the literature, see, inter alia, U.S. Pat. Nos. 2,780,604; 3,178,396; 3,770,439; 3,898,088; 4,308,335; 4,340,522; 4,424,326; 4,563,411; and 3,239,519.

The attachment of Rose-bengal, which has structural similarity to fluorescein and polymeric materials, has, also, been reported in the literature (J.Am.Chem.Soc., 97, 3741, 1985).

However, the prior art does not disclose the use of water-insoluble or partially water-soluble polymers or organic solvent-soluble polymers of ammonium and phosphonium salts with or without fluorescent molecules, as enhancers for stablized 1,2-dioxetanes.

A technique for measuring β-D-galactosidase in droplets of microscopic size using a fluorogenic substrate, 6-hydroxyfluoran-β-D-galactopyranoside was described in 1961 (Proceeding Natl. Acad. Sci., USA, 50, 1, 1963). The results obtained by this technique indicate that it is capable of detecting individual molecule of the enzyme in less than 10 hours of incubation. The Collins spray method was used to disperse a solution containing the enzyme and the substrate into droplets of 0.1 to 40µ diameter. In this method, the solution is atomized over a few drops of silicone oil places on a microscope slide coated with silicon.

Today, single molecule detection (SMD) is a well established technique. The experiment of choice in SMD is laser-induced fluorescence detection. However, there is now a broader range of practical realization for this technique. Aside from the traditional techniques of SMD in confocal volumes using highly focused laser beams, confocal and wide field microscopy on surface and nearfield microscopy have developed into powerful methods for single molecule spectroscopy. Single molecules are also detected by scanning techniques and by imaging systems and are monitored under ambient conditions and at low temperatures (Cytometry, 36, 162 (1999)). In many applications of solution-phase single-molecule detection techniques, however, there is often either insufficient signal or data throughput issues that make it nontrivial or impractical to image single-molecule fluorescence in flowing streams. Furthermore these techniques require complicated instrumentation. As detailed below the present invention demonstrates the use of an enhanced stabilized 1,2-dioxetanes system for use in single molecule detection. The present invention, also, discloses, a diluent which when used with 1,2-dioxetanes provides a chemiluminescent signal which enables detection at the single molecule level.

SUMMARY OF THE INVENTION

The present invention enables the detection of alkaline phosphatase enzyme or other enzymes at attogram level or single molecule detection in aqueous buffers utilizing a chemilluminescent system which comprises (1) a stable 1,2-dioxetane derived from a spiro-fused ketone with or without π-electrons in the ring or with carbon—carbon double bond(s) in the spiro-fused ring, (2) an polymeric enhancer or enhancers which is either, a water-insoluble, soluble in organic media, partially water-soluble, water-soluble, the polymer being derived from polymeric vinylbenzyl chloride and a trisubstituted amine or trisubstituted phosphine with or without fluorescent molecules, and (3) an enzyme diluent which stabilizes the enzyme during the reaction.

Thus, the present system may be diagrammatically illustrated as:

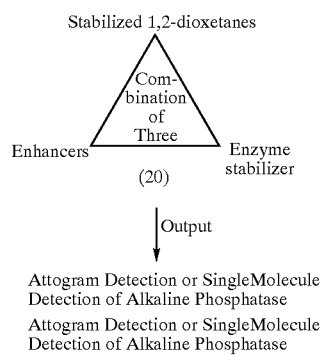

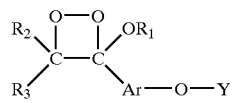

Attogram Detection or SingleMolecule Detection of Alkaline Phosphatase
Attogram Detection or SingleMolecule Detection of Alkaline Phosphatase The 1,2-dioxetanes hereof generally correspond to the formula:

(14)

wherein, (1) when Ar—O—Y and OR join together to give an aryl group substituted with an O—Y group to form a stable 1,2-dioxetane intermediate which is triggerable to form an unstable intermediate oxide, $R_2$ and $R_3$ either form (a)

which is either cyclic, polycyclic or a spiro-fused ring containing at least one carbon—carbon double bond or cabon—carbon triple bond in the ring or side chain with or without hetero atoms, or (b)

which is either cyclic, polycyclic or a spiro-fused ring containing a substituted or unsubstituted fused aromatic ring or substituted or unsubstituted aromatic ring attached by linker arms;

(2) when Ar—O—Y and $OR_1$ do not join together a) Ar is an aryl which may be phenyl, substituted phenyl, naphthyl, substituted naphthyl, anthryl, substituted anthryl and the like as well as a nonaromatic fluorescent or nonfluorescent group; Y is hydrogen, alkyl, acetate, t-butyldimethylsilyl or an enzyme or a group of enzymes cleavable group, or an antibody cleavable group; $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, linear or branched halogenated alkyl, alkylalcohol, alkylnitrile, alkylamine, alkylacid or an inorganic salt thereof, haloalkylalcohol, haloalkylnitrile, haloalkylamine, haloalkylacid or an inorganic salt, thereof, linker-flourescent molecule, linker-antibodies, linker-antigen, linker-biotin, linker-avidin, linker-protein, linker-carbohydrates or linker-lipids; $R_2$ and $R_3$ form either (i)

which is cyclic, polycyclic or a spiro-fused ring containing at least one carbon—carbon double bond or cabon—carbon triple bond in the ring or side chain with or without heteroatoms, or (ii)

which is cyclic, polycyclic or a spiro-fused ring containing substituted or unsubstituted fused aromatic ring or substituted or unsubstituted aromatic rings attached by linker arms; wherein or (iii))

which is a cyclic or polycyclic alkyl group or spiro-fused ring with or without substitution or (iv) are branched alkyl and cycloalkylgroups containing 3 to 8 carbon atoms which can contain halogens and hetero atoms in the ring or side chain thereof.

In preparing the 1,2-dioxetanes hereof, enzyme cleavable alkenes are synthesized from hydroxyalkenes and a suitable reagent. Photooxygenation of the resulting vinyl ether alkenes by well-known conventional techniques affords 1,2-dioxetanes that are easily handled compounds with the desired stability. When alkaline phosphatase or other enzymes, such as beta galactosidase and cholinesterase is used to destabilize the dioxetane, the phosphorous oxychloride is a suitable reagent, under basic conditions.

These 1,2-dioxetanes are more particularly described in the above referred to copending PCT application.

The effect of substitution on the solubility of certain polyviny benzyl chloride polymers has been described in U.S. Pat. No. 4,308,335. According to this reference, the quaternary nitrogen polymers of the reference are prepared by the reaction of polyvinylbenzyl chloride and a tertiaryamine and structure of the polymer can be shown as below:

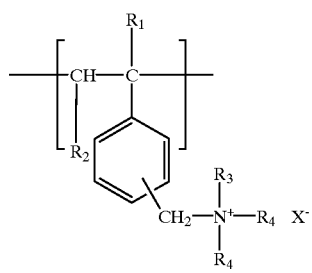
(21)

When the quaternary nitrogen of formula (20) has a long alkyl chain i.e. more than a five carbon chain, the resulting cationic polymer is insoluble in water but is soluble in organic solvents.

In the same way when polyvinylbenzyl chloride is treated with trialkylphosphine, the following polymer is obtained:

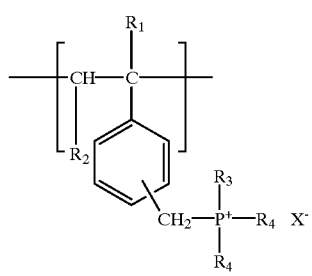
(22)

Where $R_3$, $R_4$ and $R_5$ are long chain hydrocarbons, i.e. more than five carbon atoms, the resulting cationic polymer is water-insoluble. Other water insoluble or partially water-insoluble polymers can be synthesized by the combination of two or three different trialkylphosphines. These polymers have shown excellent enhancement of chemiluminescent of stabilized 1,2-dioxetanes compared to water-soluble polymers.

As is known to those skilled in the art, the stability of the enzyme is the most important factor in the detection of biological molecules. The present invention utilizes a unique diluent or buffer based upon the composition of human blood serum. The present diluent is a tris-buffer containing proteins, metal halides such as sodium chloride, potassium chloride, magnesium chloride, zinc chloride, and the like, alcohols or polyhydric alcohols and sodium azide. The pH of the buffer is between 7.5 to 8.5. The lower concentration of alkaline phosphatase ($\cong$100 molecules of alkaline phosphatase per ml of diluent) is stable at least for one week when stored at 4° C. in this buffer.

The chemiluminescent decomposition of the 1,2-dioxetanes hereof, as noted above, preferably, can be conveniently triggered at room temperature by removing the protecting group with a fluoride ion, a base or an enzyme to generate the unstable aryl oxide 1,2-dioxetane intermediate which cleaves to the starting materials and yields intense blue or other colored luminescence light.

For a more complete understanding of the present invention reference is made to the following detailed description and accompanying examples.

DESCRIPTION OF THE PREFERRED EMBODIMENTS

As stated above chemiluminescent enzyme substrates or reagents based on 1,2-dioxetanes are well known in the literature for biological assays such as immunoassays and DNA probes. Use of these high energy compounds in biological systems requires 1,2-dioxetanes, which are thermally stable at the temperature of the enzymatic reaction and which do not undergo rapid spontaneous decomposition in an aqueous buffer. The spiro-fused adamantyl-1,2-dioxetanes hereof meet these requirements. The present 1,2-dioxetanes can be modified as substrates for various enzymes including aryl esterase, β-galactosidase, alkaline phosphatase and others.

As noted the 1,2-dioxetanes hereof correspond to the formula:

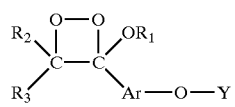
(14)

wherein, (1) when Ar—O—Y and OR join together to give an aryl group substituted with an O—Y group to form a stable 1,2-dioxetane intermediate which is triggerable to form an unstable intermediate oxide, $R_2$ and $R_3$ either form (a)

which is either cyclic, polycyclic or a spiro-fused ring containing at least one carbon—carbon double bond or cabon—carbon triple bond in the ring or side chain with or without hetero atoms, or (b)

which is either cyclic, polycyclic or a spiro-fused ring containing a substituted or unsubstituted fused aromatic ring or substituted or unsubstituted aromatic ring attached by linker arms;

(2) when Ar—O—Y and $OR_1$ do not join together

Ar is an aryl which may be phenyl, substituted phenyl, naphthyl, substituted naphthyl, anthryl, substituted anthryl and the like as well as a nonaromatic fluorescent or nonfluorescent group; Y is hydrogen, alkyl, acetate, t-butyldimethylsilyl or an enzyme or a group of enzymes cleavable group, or an antibody cleavable group; $R_1$ is selected from the group consisting of alkyl, aryl, aralkyl, alkaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, linear or branched halogenated alkyl, alkylalcohol, alkylnitrile, alkylamine, alkylacid or an inorganic salt thereof, haloalkylalcohol, haloalkylnitrile, haloalkylamine, haloalkylacid or an inorganic salt, thereof, linker-flourescent molecule, linker-antibodies, linker-antigen, linker-biotin, linker-avidin, linker-protein, linker-carbohydrates or linker-lipids; $R_2$ and $R_3$ form either (i)

which is cyclic, polycyclic or a spiro-fused ring containing at least one carbon—carbon double bond or cabon—carbon triple bond in the ring or side chain with or without heteroatoms, or (ii)

which is cyclic, polycyclic or a spiro-fused ring containing substituted or unsubstituted fused aromatic ring or substituted or unsubstituted aromatic rings attached by linker arms; wherein or (iii))

which is a cyclic or polycyclic alkyl group or spiro-fused ring with or without substitution or (iv) are branched alkyl and cycloalkylgroups containing 3 to 8 carbon atoms which can contain halogens and hetero atoms in the ring or side chain thereof. These 1,3-dioxetanes are prepared by the photooxygenation of the vinyl ether alkene, which in turn, is the reaction product of a first, ketone and a second ketone or ester.

Typically, the alkenes hereof are prepared by the reaction of (a) 2-adamantanone or other spiro-fused ketone including ketones having a π-electron in the ring with (b) a substituted aromatic ester or ketone, using titanium trichloride or tetrachloride and a reducing agent such as an active metal or lithium aluminium hydride in tetrahydrofuran (THF). This reaction is an intermolecular coupling of a ketone and an ester or ketone to form a vinyl ether using a modified McMurray procedure. Ordinarily, the reactants are present in at least stoichiometric quantities. However, excess amounts of the ester or ketone can be used. The temperatures at which the reactions as described above are those disclosed in the art.

Photo-oxygenation of the resulting vinyl ether alkene affords 1,2-dioxetanes that are easily handled compounds with the desired stability.

As noted, these 1,2-dioxetanes are more particularly described in the a forementioned copending PCT application, the disclosure of which is hereby incorporated by reference.

When these 1,2-dioxetanes react with an activating reagent or agent which removes the Y moiety, they decompose to form an aryl oxide 1,2-dioxetane intermediate of the formula:

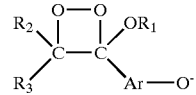

(23)

This aryl oxide 1,2-dioxetane intermediate, then, spontaneously decomposes to produce light and compounds of the formulae:

(24)

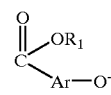

(25)

where compound (24) is the starting organic ketone and compound (25) is the residue of the starting organic ester or ketone when Ar O⁻ and $OR_1$ join together.

In practicing the present invention, compound (24) can be any one of or a mixture of adamantan-2-one, substituted adamantan-2-one, adamantan-2-one-4,5-ene, substituted adamantan-2-one-4,5-ene, 2-hydroxytricyclo[7.3.1.0$^{2,7}$] tridecan-13-one or substituted 2-hydroxytricyclo[7.3.1.0$^{2,7}$] tridecan-13-one, tricyclo(7.3.1.0$^{2,7}$]tridec-2,7-ene-13-one or substituted tricyclo[7.3.1.0$^{2,7}$]tridec-2,7-ene-13-one, bicyclo[3.3.1]nonan-9-one or substituted bicyclo[3.3.1] nonan-9-one benzonorbonen-7-one or substituted benzonorbornen-7-one, 2,4-dimethyl-3-propanone or substituted 2,4-dimethyl-3-propanone, dicyclopropyl ketone or substituted dicyclopropyl ketone, dicyclohexyl ketone or substituted dicyclohexyl ketone when compound (25) is selected from the group consisting of substituted or unsubstituted 9H-fluoren-9-one, 9H-xanthen-9-one, 2,2,2-trifluoroethyl 3-hydroxybenzoate or substituted 2,2,2-trifluoroethyl 3-hydroxybenzoate, 2-phenoxyethyl 3-hydroxybenzoate or substituted 2-phenoxyethyl 3-hydroxybenzoate, and the like. Further, the ketone of formula (23) may be selected from the group consisting of adamantan-2-one-4,5-ene, substituted adamantan-2-one-4, 5-ene, tricyclo[7.3.1.o$^{2,7}$]tridec-2,7-ene-13-one, substituted tricyclo[7.3.1.0$^{2,7}$]tridec-2,7-ene-13-one when the compound of formula (24) is alkyl or aryl 3-hydroxybenzoate or substituted alkyl or aryl 3-hydroxybenzoate.

The alkenes hereof used to prepare the present dioxetane correspond to the formula:

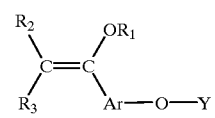

(26)

wherein $R_1$, $R_2$, $R_3$, Y and Ar are as described above,

These alkenes are prepared by the coupling of the above-described ketones and esters or ketones.

Generally, the intermolecular coupling reaction between the ketone and the ester or ketone is carried out at a temperature ranging from about 25° C. to about 85° C. and, perferably, from about 45° C. to about 65° C. A stoichiometric excess of either the ester or ketone may be used.

The coupling reaction is carried out in the presence of suitable solvents and active metals as described in the prior art denoted above, the disclosures of which are hereby incorporated by reference.

After the alkene is obtained it is, then, photo-oxidized to form the stable, triggerable 1,2-dioxetane hereof. These 1,2-dioxetanes can, then, be destablized or triggered by the reaction with a base, an acid, an enzyme and/or inorganic or organic catalyst and/or electron donor source in the presence or absence of a fluorescent compound, as described in the literature or above cited prior art.

As noted herein above the present invention provides a unique enhancer for the 1,2-dioxetanes when triggered by an alkaline phosphatase enzyme, when diluted in a modified diluent in a aqueous buffer. The present enhancers are polymers of annomium or phosphonium salts which may contain fluorescent molecules. The polymers hereof may be water-soluble, water-insoluble or partially water-soluble or soluble only in an organic solvent. Typically, the degree of solubility in water or in an organic solvent will depend on the chain length of the ammonium salt or the phosphonium salt. Thus, typically, insoluble polymers will have at least six carbon atoms in the carbon chain. Preferably, the polymers contemplated for use herein are derivatives of polyvinylbenzyl chloride.

In accordance herewith and as noted above, the present invention provides the use of water-insoluble, water-soluble or partially water-soluble polymers as an enhancer to enhance the chemiluminescent of 1,2-dioxetanes when triggered by alkaline phosphatase enzyme (diluted in modified diluent) or other enzymes which maybe detected with the present system or substrate include beta galactosidase and cholinesterase in aqueous buffer.

Water-insoluble and partially water-soluble ammonium salts and phosphonium salts of polyvinylbenzyl chloride are prepared by known techniques. Insoluble polymers such as polyvinylbenzyltrioctylphosphonium chloride and polyvinylbenzyltrioctylammonium chloride are prepared by reacting polyvinylbenzyl chloride with trioctylphosphine and trioctylamine, respectively, using dimethylformamide as a solvent. Partially water-soluble polymers are synthesized by the reaction of polyvinylbenzyl chloride containing trioctylphosthine and tributylphosphine (80:20) in dimethyl formamide or trioctylamine and tributylamine (80:20) in dimethylformamide. Fluorescent polymers are obtained by heating fluorescein and polyvinylbenzyl chloride in dimethyl formamide at 70–75° C. for 36–48 hours and then, after cooling, adding trioctylphosphine and tributylamine (80:20) into the reaction mixture. Water-soluble polymers are synthesized by the reaction of polyvinyl benzyl chloride and a lower alkyl chain substituted phosphine or amine. These polymers were crystallized by dimethyformamide and anhydrous ether.

Among the useful products, in preparing a water-insoluble or partially water-soluble ammonium salts or phosphonium salts are the reaction product of polyvinyl benzyl chloride with trioctylphosphine or trioctylamine. In preparing insoluble polymers usually a solvent such as, dimethylformamide, is deployed as a solvent. Partially water-soluble polymers may be made, for example, by the reaction of the polyvinyl benzyl chloride with a mixture of higher molecular weight and lower molecular wieght or higher chain and lower chain substituted phosphines such as a mixture of trioctylphosphine and tributylphosphine in ratio of about 4:1; similarly, the ammonium salt may be prepared with a mixture of trioctylamine or tributylamine in a similar weight to weight ratio.

Generally, in preparing these molecules they react at a temperature of about 20° to about 100° C. for a period ranging from about 10 to about 500 hours. Typically, an excess of trisubstituted phosphine or amine is used compared to polyvinyl benzyl chloride.

Other useful water-soluble, partially-water soluble and water-insoluble polymers include, for example, copolymers of vinyl benzyl chloride and 2-vinylnaphthalene with or without bifunctional linker arms.

Other, useful organic solvents include but not limited to, for example; dimethyformamide, dimethyl sulfoxide, alcohols or other polar solvents or combination of solvents which can dissolve the polymer.

In preparing water-soluble polymers, generally, lower alkyl trisubstituted phosphine or amine is used.

Enzyme Diluent

The third component of the system, and as noted hereinabove, is an enzyme diluent. The enzyme diluent is an aqueous solution having a pH ranging from about to pH 7 to about pH10 preferable about pH 7.5 to about pH 8.5 and, essentially, correlates to and contains many of the components found in blood.

Generally, the diluent comprises an aqueous mixture of a buffer and components such as alkaline metal halides: metals such as sodium, potassium, magnesium, zinc but not limited to, as well as alcohods and amine-based salts.

Amongst the useful buffers are, for example tris (hydroxymethylaminomethane, diethanolamine, Triethanolamine, 2-amino0-2-methyl-1-propanol, as well as mixtures thereof.

Suitable monovalent metal halides include for example sodium chloride, potassium chloride as well as mixtures thereof. Suitable divalent metals, such as magnesium, zinc or the like which are deployed as the metal halide salt thereof, such as magnesium chloride, zinc chloride and the like as well as mixtures thereof.

Suitable alcohols include, for example, ethyl alcohol, propyl alcohols, butyl alcohols, ethylene glycol, ethylene glycol methyl ether, glycerol.

Similarly, useful proteins include, for example, blood proteins from human or animal sources such as BSA, HSA and proteins from plant sources such as trypsin inhibitor.

The pH of the buffer is adjusted through the use of suitable acids such as hydrochloric or acetic acid.

The diluent is prepared by admixing the components together in deionized water to form the aqueous solution thereof.

In preparing a system for utilization, generally, the solution hereof, will comprise from about 0.005 to about 0.05 percent, by weight, of the 1,2-dioxetane, from about 0.001 to about 0.5 percent by weight of the enhancer and from about 0.05 to about 10 percent of the diluent with enzyme. Preferably, the system will contain from about 0.01 to about 0.03 percent, by weight, of dioxetane, from about 0.01 to about 0.05 percent, by weight, of the enhancer and from about 0.5 to 5.0 percent by weight, of the diluent with enzyme, based upon the total weight of the composition. The balance of the system is deionized water.

The present composition may be used to detect and quantitate various biological molecules including haptenes, antigen, an antibodies for use in immunoassays, proteins utilizing western blotting, DNA and RNA detection using southern and northern blotting, respectively as well as for use in DNA sequencing and other related applications.

It should be further noted herein that although the present enhancer and diluent have been described in connection with the specific 1,2-dioxetanes, it should be noted that the enhancer as well as the diluent, as stand alone items, can be used in conduction with other 1,2-dioxetanes for enhancing and for diluting same. Thus, the utilization of the enhancer and as well as the diluent are not limited to the use in conduction with the preferred 1,2-dioxetanes hereof.

Following are specific non-limiting examples of the present invention. In the examples all parts are by weight or percentages unless expressly stated to be otherwise.

In the examples certain components were used throughout, as follows:

(a) The enzyme diluent was prepared from the following components in deionized water and based on a weight percent basis:
- (1) Tris (hydroxymethyl)aminomethane: 0.1 to 40 percent
- (2) Sodium chloride: 0.1 to 25 percent
- (3) Potassium chloride: 0.01 to 5 percent magnesium chloride: 0.001 to 1.0 percent
- (4) Zinc chloride: 0.0001M to 0.1 percent
- (5) Alcohols: 0.1 to percent
- (6) Proteins: 0.01 to 7.5 percent
- (7) Sodium azide: 0.1 to 2.5 percent The pH of the buffer ranged from pH 7.0 to pH 10.0

Three different sources of alkaline phosphatase were used (1). Sigma Chemical Company, Catalog #P7923, lot #128H1210 and 6,510 U/mg of protein, (2). Worthington Biochemical Corporation, 2000 U/vial, 2,800 U/mg protein and lot #69k3248, and (3). Roche Diagnostic Corporation (Boehringer Mannheim), 2000 U/mg protein and lot #85382422.

Each of these enzymes were diluted in the above defined diluent in which the enzyme is stable for an extended period of time at room temperature. For each source of enzyme, the concentration of alkaline phosphatase was adjusted to 0.27 mg/ml of the buffer. This solution contains 2.7 parts of alkaline phosphatase in 10,000 parts of modified buffer (dilution #1). Then 100 µl of the dilution #1 of alkaline phosphatase solution is further diluted in 900 µl of the buffer to yield dilution #2. This solution contains 2.7 parts of alkaline phosphatase in 100,000 parts of buffer (dilution #2). Next 100 µl of this dilution #2 was added to 900 µl of the enzyme diluent to form dilution #3. The dilution was continued to prepare dilutions #4, #5, #6, #7, #8, #9, #10, #11, #12, #13 and #14. Dilution #14 has the enzyme concentration of $2.7 \times 10^{-14}$ mg/ml or $2.7 \times 10^{-17}$ g/ml of buffer. In other words, 10 µl of dilution #14 has $2.7 \times 10^{-19}$ g of alkaline phosphatase. In the kinetic experiments, 10 µl of enzyme was used in 200 µl of the dioxetane sample from dilutions #14, #13, #12 and #11. The molecular weight of alkaline phosphatase enzyme is considered as being between 140,000 to 160,000, as reported in the literature and depending on the amounts of sugar units it contains. Using an assumed molecular weight of 160,000 and divided by the Avogadro's number which is $6.022 \times 10^{23}$, the weight of one molecule of alkaline phosphatase can be calculated as at least $2.66 \times 10^{-19}$ g or 0.266 attogram. The diluted samples of enzyme (#14) at least more than one molecule of alkaline phosphatase is present.

EXAMPLE I

Using a suitable container, at ambient temperature, into 1000 parts of a 1 M solution of the tris buffer (pH 9.5 to 9.7) was dissolved 0.2 parts of [(4-Methoxy)-4-(3phosphoryloxy4-chlorophenyl)]spiro[1,2-dioxetane-3,3-tricyclo[$7.3.1,0^{2,7}$]tridec-2,7-ene]disodium salt.

Polyvinylbenzyltrioctylphosphonium chloride (0.7 parts) was dissolved in 100 parts of dimethylsulfoxide. To 100 parts of the 1,2-dioxetane solution two (2) parts of the polymer solution was added and mixed properly.

Then two hundred microliters (0.200 mL) of 1,2-dioxetane in the buffer was transferred into a tube (75×12 mm) and background luminescence was recorded in a Monolight 2010 single tube luminometer. Then, 10 µl of each enzyme, as dilution #14, was added and the output light intensity was recorded at a 60 second of interval of time. The results are shown herewith:

FIG. 1 is a graph showing a comparison of the chemiluminescence of each enzyme #14 dilution. Each dilution contains 0.27 attogram or at least a single molecule of alkaline phosphatase when 10 µl of the enzyme was used in 200 µl of the 1,2-dioxetane sample in tris buffer. FIG. 1 shows that single molecule of alkaline phosphatase can be detected in solution, when using a modified enzyme diluent, a water-insoluble polymer and a stabilized 1,2-dioxetane having π-electrons in their stabilizing ring which stabilizes the dioxetane ring.

EXAMPLE II–IV

Following the procedures of EXAMPLE I, other dilutions were prepared and the results were plotted as follows:

FIG. 2 is a graph showing a comparison of the chemiluminescence of each of the three #13 diluted enzymes. Each dilution #13 has at least 10 molecules of alkaline phosphatase FIG. 3 is a graph showing a comparison of the chemiluminescence of each of the three #12 diluted enzymes. Each dilution #12 has at least 100 molecules of alkaline phosphatase.

FIG. 4a and 4b are graphs of the chemiluminescence of the Sigma enzyme diluted to dilutions #11, #12, #13 and #14, enzyme dilutions #11, #12, #13, and #14 have at least 1, 10, 100 and 1000, molecules of alkaline phosphatase respectively.

EXAMPLE V

Single molecule detection was tested in microtiter plates using Labsystem Fluoroskan Ascent FL luminometer. The enzyme used in this experiment was obtained from Sigma Chemical Company, as identified in Example I.

Ten µl of enzyme diluent, as a base line, 10 µl of diluted enzyme #14, 10 µl of diluted enzyme #13, 10 µl of diluted enzyme #12 and 10 µl of diluted enzyme #11 was added to each of two sets of a three well of a 96 well microtiter plate, Next, in each well, 200 µl of the enzyme substrate was added and the microtiter plate was incubated at 37° C. for 25 minutes. The luminescence from each well was recorded. The following results were obtained.

| Enzyme # | Well #1 | Well #2 | Well #3 |
|---|---|---|---|
| Enzyme diluent | 117.0 | 115.4 | 121.6 |
|  | 121.6 | 124.3 | 137.5 |
| Enzyme #14 | 529.3 | 554.6 | 568.5 |
|  | 579.1 | 575.8 | 604.7 |

-continued

| Enzyme # | Well #1 | Well #2 | Well #3 |
| --- | --- | --- | --- |
| Enzyme #13 | 4246 | 4195 | 4430 |
|  | 4148 | 4278 | 4508 |
| Enzyme #12 | 31308 | 31977 | 30545 |
|  | 32115 | 31865 | 33558 |
| Enzyme #11 | 78751 | 79487 | 81815 |
|  | 80561 | 77577 | 81306 |

When this experiment was repeated using a Monolight 2010 single tube (75×12) luminometer, similar results were obtained.

In supporting the findings, the structures of the resulting compounds were confirmed by Nuclear Magnetic Resonance (NMR). NMR spectra were recorded on a General Electric QE 300 spectrometer in desired solvents using tetramethylsilane as an internal standard. Chemiluminescence kinetics were performed on a Monolight 1500 at room temperature. The purity of the materials were checked by TLC on silica gel plate. Melting points were measured in a MEL-TEMPII capillary melting point apparatus and are uncorrected. All the alkenes were dissolved in a mixture of methylene chloride and methanol and photooxidized by irradiation with 1000-W sodium lamp under bubbled oxygen at ice-water temperature in the presence of polystyrene-bound Rose Bengal.

Light intensity measurements were made using a Monolight 2010 single tube (75×12 mm) luminometer. All analytical results are the average of at least duplicate measurements. The luminescence was recorded in 60 seconds intervals.

As a detection formulation, the composition hereof defines a substrate. Thus in use, a quantity of known biological molecule such as polyclonal or monoclonal antibody, antigen, hapten-protein, protein, DNA, RNA or the like is deposited or coated onto a support. The support or base is a solid surface which may be of any suitable material such as glass or plastic. The material may be in the form of a microtiter plate or a tube, a bead, a membrane or the like. After the coating is applied, the sample to be tested is, then, exposed to the coating, followed thereafter by further sequencing. This can be illustrated as follows:

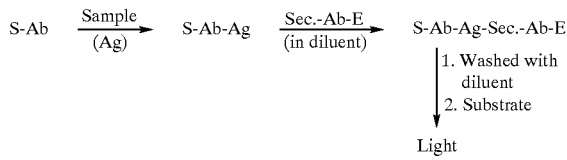

Where S is the support, Ab is an antibody, Ag is an antigen, Sec. Ab is a secondary antibody, E is an enzyme and the substrate is the present formulation. As illustrated, S-Ab-Ag-Sec.Ab-E defines a probe which is used to detect the presence or absence of a suspected or unknown molecule by cleaving the Y moiety with the enzyme probe. In other other words if the secondary antibody does not attach to to the antigen or if the antigen is not present, then no light is giving off.

Other useful probes include those which correspond to the following:
S-Ag-Ab-Sec.Ab-E;
S-protein-hapten-Ab-E;
S-protein-Ab-E;
S-DNA-biotin-avidin-E; and
S-RNA-biotin-avidin-E.

It is to be appreciated that and in accordance herewith that, and as noted above, the enzyme E can be alkaline phosphatase, β-galactosidase or cholinesterase.

Thus, the present invention may be used for, inter alia, labeling haptens, antibodies, proteins, avidin, streptavidin and DNA and RNA for enzyme immunoassays, immunocytochemistry, immuno-blotting and DNA detection. In a commercial embodiment, hereof, the present substrate may be packaged with a support, as well as, optionally, with an antibody, antigen, secondary antibody, etc. in a separate containers.

What is claimed is:

1. A chemiluminescence detection system, comprising:
   (a) an enzyme triggerable stable chemiluminescent 1,2-dioxetane corresponding to the formula:

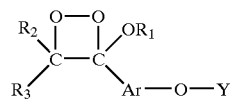

wherein $R_2$ and $R_3$ are each organic groups which when combined together form an unsaturated organic group or when uncombined at least one of the $R_2$ and $R_3$ contains an unsaturated carbon double bond or triple bond and Y is an enzyme cleavable group and $R_1$ is either a substituted or unsubstituted aryl, alkyl, aralkyl, alkaryl, alkene or alkyne, and further wherein when Ar—O—Y and OR join together to give an aryl group substituted with an O—Y group to form a stable 1,2-dioxetane intermediate which is triggerable to form an unstable intermediate oxide, $R_2$ and $R_3$ form (i)

which is either cyclic, polycyclic or a spiro-fused ring containing at least one carbon—carbon double bond or cabon-carbon triple bond in the ring or side chain with or without hetero atoms,
   (a) an enhancer, and
   (b) an enzyme diluent or stabilizer.

2. The system of claim 1 wherein the 1,2 dioxetane is [(4-methoxy)-4-(3-phosphoryloxy-4-chlorophenyl)]spiro[1,2dioxetane-3,13'-tricyclo[7,3,1,0$^{2,7}$]tridec-2,7-ene], disodium salt.

3. The system of claim 1 wherein the enzyme diluent comprises an aqueous mixture of:
   (a) a metal halide,
   (b) an alcohol,
   (c) an amine-based salt,
   (d) a blood or plant protein or mixtures thereof, and
   wherein the diluent has a pH of from about pH 7 to about pH 10, the diluent corresponding to blood components, and further wherein the system is enzyme triggerable at single molecule detection levels.

4. A method of chemiluminescence detection, which comprises; contacting the system of claim 1 with an enzyme selected from the group consisting of alkaline phosphatase, beta galactosidase, and cholinesterase.

5. The system of claim 1 wherein the chemiluminescent 1,2-dioxetane has the following structure

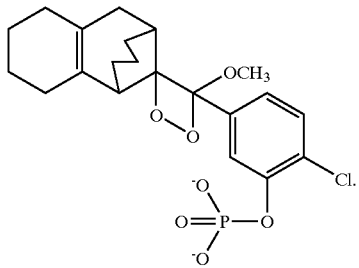

6. The system of claim 5 wherein the enhancer is selected from the group consisting of an ammonium or a phosphonium polymeric salt and mixtures thereof.

7. The system of claim 6 wherein the polymer salt comprises a fluorescent molecule.

8. The system of claim 6 wherein the enhancer is a water-soluble polymeric compound prepared by reacting polyvinylbenzyl chloride with either tributylphosphine or tributylamine to form the phosphonium salt or ammonium salt, respectively.

9. The system of claim 6, wherein the enhancer is partially water-soluble, the enhancer being prepared by the reaction of polyvinyl benzyl chloride with either a 4:1 weight ratio mixture of (a) trioctylphosphine and tributylphosophine or (b) trioctylamine and tributylamine.

10. The system of claim 6 wherein the enhancer is a water-insoluble polymeric compound prepared by reacting polyvinylbenzyl chloride with either trioctylphosphine or trioctytylamine to form the phosphonium salt or ammonium salt, respectively.

11. The system of claim 10 wherein the polymer comprises a fluorescent molecule.

* * * * *